United States Patent
Marinangeli et al.

(10) Patent No.: US 6,521,804 B1
(45) Date of Patent: Feb. 18, 2003

(54) PROCESS FOR PRODUCING PHENYL-ALKANES USING DUAL ZONES

(75) Inventors: Richard E. Marinangeli, Arlington Heights, IL (US); R. Joe Lawson, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/939,059

(22) Filed: Aug. 24, 2001

(51) Int. Cl.⁷ .............................. C07C 5/107; C07C 2/66
(52) U.S. Cl. ..................... 585/323; 585/449; 585/467; 585/455
(58) Field of Search .................. 585/323, 449, 585/467, 455

(56) References Cited

U.S. PATENT DOCUMENTS

| | | | |
|---|---|---|---|
| 4,301,317 A | 11/1981 | Young | 585/455 |
| 5,196,574 A | 3/1993 | Kocal | 562/94 |
| 5,276,231 A | 1/1994 | Kocal et al. | 585/323 |
| 5,302,732 A | 4/1994 | Steigleder et al. | 554/98 |
| 5,344,997 A | 9/1994 | Kocal | 568/628 |
| 5,777,187 A | 7/1998 | Knifton et al. | 585/449 |
| 6,090,993 A | 7/2000 | Gupta et al. | 585/827 |
| 6,133,492 A * | 10/2000 | Anantaneni | 585/323 |

FOREIGN PATENT DOCUMENTS

| | | |
|---|---|---|
| WO | WO 99/05082 | 2/1999 |
| WO | WO 99/05084 | 2/1999 |
| WO | WO 99/05241 | 2/1999 |
| WO | WO 99/05243 | 2/1999 |
| WO | WO 99/07656 | 2/1999 |
| WO | WO 00/23404 | 4/2000 |
| WO | WO 00/23405 | 4/2000 |
| WO | WO 00/23548 | 4/2000 |
| WO | WO 00/23549 | 4/2000 |

OTHER PUBLICATIONS

*Handbook of Petroleum Refining Processes* edited by Robert A. Meyers, (McGraw–Hill, New York, $2^{nd}$ Ed., 1997), pp. 1.53 to 1.66 and pp. 5.11 to 5.19.

Méraudeau, P. et al. "Zeolite based catalysts for linear alkylbenzene production: Dehydrogenation of long chain alkanes and benzene alkylation" *Catalysis Today* 38 (1997) 1997 Elsevier Science B.V. pp. 243–247.

Sivasanker, S. et al. "Distribution of Isomers in the Alkylation of Benzene with Long–Chain Olefins over Solid Acid Catalysts" *Journal of Catalysis* 138 (1992) pp. 386–390.

S. Sivasanker et al., "Shape Selective Alkylation of Benzene with Long Chain Alkenes Over Zeolites" *New Frontiers in Catalysis: Proceedings of the $10^{th}$ International Congress on Catalysis* Jul. 19–24, 1992 Budapest, Hungary 1993 Elsevier Science Publishers B.V. Editors: L. Guzci et al. pp. 397–408.

* cited by examiner

*Primary Examiner*—Thuan D. Dang
(74) *Attorney, Agent, or Firm*—John G. Tolomei; James C. Paschall; Michael A. Moore

(57) ABSTRACT

The present invention is a process for producing phenyl-alkanes by alkylation of an aryl compound with an olefinic compound and which uses a mordenite catalyst and a silica-alumina catalyst. This invention is also a process that sulfonates phenyl-alkanes having lightly branched aliphatic alkyl groups to produce modified alkylbenzene sulfonates. In addition, this invention is the compositions produced by these processes, which can be used as detergents having improved cleaning effectiveness in hard and/or cold water while also having biodegradability comparable to that of linear alkylbenzene sulfonates, as lubricants, and as lubricant additives. This invention is moreover the use of compositions produced by these processes as lubricants and lubricant additives.

25 Claims, No Drawings

PROCESS FOR PRODUCING PHENYL-ALKANES USING DUAL ZONES

FIELD OF THE INVENTION

The invention relates to a process for the selective production of phenyl-alkane and phenyl-alkane sulfonate compositions, to the particular phenyl-alkane are phenyl-alkane sulfonate compositions produced therefrom, and to uses of those compositions.

BACKGROUND OF THE INVENTION

More than thirty years ago, many household laundry detergents were made of branched alkylbenzene sulfonates (BABS). BABS are manufactured from a type of alkylbenzenes called branched alkylbenzenes (BAB). Alkylbenzenes (phenyl-alkanes) refers to a general category of compounds having an aliphatic alkyl group bound to a phenyl group and having the general formula of $(m_i\text{-alkyl}_i)_i$-n-phenyl-alkane. The aliphatic alkyl group consists of an aliphatic alkyl chain, which is referred to by "alkane" in the $(m_i\text{-alkyl}_i)_i$-n-phenyl-alkane formula. Of the chains of the aliphatic alkyl group, the aliphatic alkyl chain is the longest straight chain that has a carbon bound to the phenyl group. The aliphatic alkyl group may also consist of one or more alkyl group branches, each of which is attached to the aliphatic alkyl chain and is designated by a corresponding "$(m_i\text{-alkyl}_i)_i$" in the $(m_i\text{-alkyl}_i)_i$-n-phenyl-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $m_i$ of the aliphatic alkyl chain. The phenyl group is attached to the aliphatic alkyl group, specifically to carbon number n of the aliphatic alkyl chain. The aliphatic alkylation chain is numbered from one end to the other, the direction being chosen so as to give the lowest number possible to the position of the phenyl group.

The standard process used by the petrochemical industry for producing BAB consists of oligomerizing light olefins, particularly propylene, to branched olefins having 10 to 14 carbon atoms and then alkylating benzene with the branched olefins in the presence of a catalyst such as HF. Although the product BAB comprises a large number of alkyl-phenyl-alkanes having the general formula $(m_i\text{-alkyl}_i)_i$-n-phenyl-alkane, two examples of BAB are m-alkyl-m-alkyl-n-phenyl-alkanes where m≠n, and m-alkyl-m-phenyl-alkanes where m≧2.

The most prominent common characteristic of BAB is that, for a large proportion of BAB, there is attached to the aliphatic alkyl chain of BAB generally at least one alkyl group branch, and more commonly three or more alkyl group branches. BAB thus has a relatively large number of primary carbon atoms per aliphatic alkyl group, since the number of primary carbon atoms per aliphatic alkyl group in BAB equals the number of alkyl group branches per aliphatic alkyl group plus either one if n=1, or two if n≧2, provided that the alkyl group branches themselves are unbranched. If any alkyl group branch itself is branched, then the aliphatic alkyl group in BAB has even more primary carbon atoms. Thus the aliphatic alkyl group in BAB usually has three, four, or more primary carbon atoms. As for the alkyl group branches of the aliphatic alkyl group in BAB, each alkyl group branch is often a methyl group branch, although, ethyl, propyl, or higher alkyl group branches are possible.

Another typical characteristic of BAB is that the phenyl group in BAB can be attached to any non-primary carbon atom of the aliphatic alkyl chain. Except for 1-phenyl-alkanes whose formation is known to be disfavored due to the relative instability of the primary carbenium ion and neglecting the relatively minor effect of the branches of the branched paraffins, the oligomerization step produces a carbon-carbon double bond that is randomly distributed along the length of the aliphatic alkyl chain, and the alkylation step nearly randomly attaches the phenyl group to a carbon along the aliphatic alkyl chain. Thus, for example, a BAB that has an aliphatic alkyl chain having 10 carbon atoms would be expected to be an approximately random distribution of 2-, 3-, 4-, and 5-phenyl-alkanes, and the selectivity of a BAB process to 2-phenyl alkane would be 25 if the distribution was perfectly random, but is often between about 10 and about 40.

A third common characteristic of BAB is that one of the carbons of the aliphatic alkyl group is a quaternary carbon. The quaternary carbon may, or may not, be the carbon in the aliphatic alkyl group that is bonded by a carbon-carbon bond to a carbon in the phenyl group. When a carbon atom on the alkyl side chain is not only attached to two other carbons on the alkyl side chain and to a carbon atom of an alkyl group branch but is also attached to a carbon atom of the phenyl group, the resulting alkyl-phenyl-alkane is referred to as a "quaternary alkyl-phenyl-alkane" or simply a "quat." Thus, quats comprise alkyl-phenyl-alkanes having the general formula m-alkyl-m-phenyl-alkane. If the quaternary carbon is the second carbon atom numbered from an end of the alkyl side chain, the resulting 2-alkyl-2-phenyl-alkane is referred to as an "end quat." If the quaternary carbon is any other carbon atom of the alkyl side chain, as in the second BAB example, then the resulting alkyl-phenyl-alkane is referred to as an "internal quat." In known processes for producing BAB, a relatively high proportion, typically greater than 10 mol-%, of the BAB is internal quats.

About thirty years ago it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured worldwide. LABS are manufactured from another type of alkylbenzenes called linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid catalyst. LAB are phenyl-alkanes comprising a linear aliphatic alkyl group and a phenyl group and have the general formula n-phenyl-alkane. LAB has no alkyl group branches, and consequently the linear aliphatic alkyl group normally has two primary carbon atoms (i.e., n≧2). Another characteristic of LAB that is produced by the standard LAB process is that the phenyl group in LAB is usually attached to any secondary carbon atom of the linear aliphatic alkyl group. In LAB produced using HF catalyst the phenyl group is slightly more likely to attach to a secondary carbon near the center as opposed to near the end of the linear aliphatic alkyl group, while in LAB produced by UOP's solid catalyst Detal™ process approximately 25–35 mol-% of n-phenyl-alkanes are 2-phenyl-alkanes.

Over the last few years, other research has identified certain modified alkylbenzene sulfonates, which are referred to herein as MABS, which are different in composition from all alkylbenzene sulfonates used currently in commerce, including BABS and LABS, and from all alkylbenzene sulfonates produced by prior alkylbenzene processes, including those which alkylate aromatics using catalysts such as HF, aluminum chloride, silica-alumina, fluorided silica-alumina, zeolites, and fluorided zeolites. MABS also differ from these other alkylbenzene sulfonates by having improved laundry cleaning performance, hard surface cleaning performance, and excellent efficiency in hard and/or cold water, while also having biodegradability comparable to that of LABS.

MABS can be produced by sulfonating a third type of alkylbenzenes called modified alkylbenzenes (MAB), and the desired characteristics of MAB are determined by the desired solubility, surfactancy, and biodegradability properties of MABS. MAB is a phenyl-alkane comprising a lightly branched aliphatic alkyl group and a phenyl group and has the general formula $(m_i\text{-alkyl}_i)_i$-n-phenyl-alkane. MAB usually has only one alkyl group branch, and the alkyl group branch is a methyl group, which is preferred, an ethyl group, or an n-propyl group, so that, where there is only one alkyl group branch and n≠1, the aliphatic alkyl group in MAB has three primary carbons. A preferred MAB is a monomethyl-phenyl-alkane. However, the aliphatic alkyl group in MAB may have two primary carbon atoms if there is only one alkyl group branch and n=1, or, if there are two alkyl group branches and n≠1, four primary carbons. Thus, the first characteristic of MAB is that the number of primary carbons in the aliphatic alkyl group in MAB is intermediate between that in BAB and that in LAB. Another characteristic of MAB is that it contains a high proportion of 2-phenyl-alkanes, namely that from about 40 to about 100% of phenyl groups are attached selectively to the second carbon atom as numbered from an end of the alkyl side chain.

A third characteristic of MAB alkylate is that the MAB has a relatively low proportion of end quats. It is believed that many end quats produce MABS that show slower biodegradation than that of LABS, even though reportedly some end quats such as 2-methyl-2-phenyl-undecane produce MABS that show biodegradation similar to that of LABS. (See the results of biodegradation experiments for sodium 2-methyl-2-undecyl [$C^{14}$] benzenesulfonate in a porous pot activated sludge treatment in the article entitled "Biodegradation of Coproducts of Commercial Linear Alkylbenzene Sulfonate," by A. M. Nielsen et al., in Environmental Science and Technology, Vol. 31, No. 12, 3397–3404 (1997).) A relatively low proportion, typically less than 10 mol-%, of MAB is end quats.

Since 2-phenyl-alkanes are a preferred component of MAB while end quats are not, and since all end quats are also 2-phenyl-alkanes, it follows that another characteristic of MAB is that a high proportion, typically from about 40 to about 100%, of MAB is nonquaternary 2-phenyl-alkanes.

A final characteristic of the MAB alkylate is that the MAB has a relatively low proportion of internal quats. Some internal quats such as 5-methyl-5-phenyl-undecane produce MABS that has shown slower biodegradation than LABS, as shown in the article by Nielsen et al. A relatively low proportion, typically less than 10 mol-%, of MAB is internal quats.

Because of the advantages of MABS over other alkylbenzene sulfonates, catalysts and processes are sought that selectively produce MAB. As suggested by the foregoing, two of the chief criteria for an alkylation process for the production of MAB are selectivity to nonquaternary 2-phenyl-alkanes and selectivity away from end quaternary phenyl-alkanes. Prior art alkylation processes for the production of LAB using catalysts such as aluminum chloride or HF are incapable of producing MAB having the desired nonquaternary 2-phenyl-alkane selectivity and end quat selectivity. In these prior art processes, when lightly branched olefins (i.e., olefins that have essentially the same light branching as that of the aliphatic alkyl group of MAB) react with benzene, quaternary phenyl-alkanes selectively form. One reaction mechanism that accounts for such selective quaternary phenyl-alkane formation is that the delinearized olefins convert, to various extents, into primary, secondary, and tertiary carbenium ion intermediates. Of these three carbenium ions, tertiary carbenium ions are the most stable, and because of their stability, are the most likely to form and react with benzene, thus forming a quaternary phenyl-alkane.

Many alkylation catalysts have been proposed for producing MAB, including zeolites having a zeolite structure type selected from the group consisting of BEA, MOR, MTW, and NES. Such zeolites include mordenite, ZSM-4, ZSM-12, ZSM-20, offretite, gmelinite, beta, NU-87, and gottardiite. Nonzeolitic alkylation catalysts, such as fluorided silica-aluminas, have also been proposed. Nevertheless, the selectivity to nonquaternary 2-phenyl-alkanes and selectivity away from end quaternary phenyl-alkanes for processes that use any one of these catalysts has been unsatisfactory for commercialization. So, processes for the production of MAB are sought that have greater selectivity to nonquaternary 2-phenyl-alkanes and selectivity away from end quaternary phenyl-alkanes.

SUMMARY OF THE INVENTION

In one aspect, this invention is a process for the production of phenyl-alkanes, in particular modified alkylbenzenes (MAB), by alkylation of an aryl compound with an olefinic compound, which uses a mordenite catalyst and a silica-alumina catalyst. The objective of this aspect of the invention is to provide a process for the production of MAB that has greater selectivity to nonquaternary 2-phenyl-alkanes and selectivity away from end quaternary phenyl-alkanes. This invention, when used for detergent alkylation, produces detergents that meet the increasingly stringent requirements of nonquaternary 2-phenyl-alkanes selectivity and end quaternary phenyl-alkane selectivity for the production of modified alkylbenzenes (MAB). Thus, in another aspect of this invention, the MAB, in turn, can be sulfonated to produce modified linear alkylbenzene sulfonates (MABS), which have improved cleaning effectiveness in hard and/or cold water while also having biodegradability comparable to that of linear alkylbenzene sulfonates. Accordingly, in one aspect, this invention is a process for producing phenyl-alkanes. An aryl compound and a monoolefin contact a first catalyst comprising mordenite operating at first reaction conditions. The monoolefin has from about 8 to about 28 carbon atoms, 3 or 4 primary carbon atoms, and no quaternary carbon atoms. The first reaction conditions are sufficient to alkylate the aryl compound with the monoolefin and thereby form a phenyl-alkane. A first reaction product comprising the phenyl-alkane is recovered. The first reaction product is contacted with a second catalyst comprising silica-alumina operating at second reaction conditions. A second reaction product comprising a phenyl-alkane having one aryl portion and one aliphatic alkyl portion containing from about 8 to about 28 carbon atoms is recovered from the process. The phenyl-alkane in the second reaction product has 2, 3, or 4 primary carbon atoms and no quaternary carbon atoms except for any quaternary carbon atom bonded by a carbon-carbon bond with a carbon atom of the aryl portion. The process has a selectivity to nonquaternary 2-phenyl-alkanes of from 40 to 100 and a selectivity to end quaternary phenyl-alkanes of less than 10 based on the second reaction product.

In another aspect, this invention is the MAB and MABS compositions produced by the processes of this invention. It is believed that the MAB and MABS produced by the process of this invention are not necessarily the products that would be produced by the prior art processes that do not employ both a mordenite catalyst and a silica-alumina catalyst, because of the selectivity toward nonquaternary 2-phenyl-alkanes and the selectivity away from end quaternary phenyl-alkanes. On sulfonation, the MABS product of the present invention could likewise tend to have more desirable characteristics than that of the prior art processes. Thus, for a given combination of feedstocks, the processes of this invention could produce particular MAB and MABS products having aliphatic alkyl chain with specially tailored extents of isomerization that are not necessarily the same as those of the prior art processes.

This invention is, in another of its aspects, the use of MAB and MABS produced by the process of this invention as a lubricant and as a lubricant additive, respectively.

Additional aspects and embodiments are described in the following description of this invention.

INFORMATION DISCLOSURE

LAB processes are described in the book edited by Robert A. Meyers entitled *Handbook of Petroleum Refining Processes*, (McGraw-Hill, New York, Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

PCT International Publication Nos. WO 99/05082, WO 99/05084, 99/05241, and WO 99/05243, all four of which were published on Feb. 4, 1999, and which are incorporated herein by reference, disclose alkylation processes for uniquely lightly branched or delinearized alkylbenzenes. PCT International Publication No. WO99/07656, published on Feb. 18, 1999, which is incorporated herein by reference, discloses processes for such alkylbenzenes using adsorptive separation.

U.S. Pat. No. 5,276,231 (Kocal et al.) describes a process for the production of linear alkylaromatics with selective removal of aromatic by-products of the paraffin dehydrogenation zone of the process. In U.S. Pat. No. 5,276,231, paraffins from the paraffin column of the alkylation zone are recycled to the reactor of the dehydrogenation zone, with or without selective hydrogenation of any monoolefins in the paraffin recycle stream. U.S. Pat. No. 5,276,231 also teaches the selective hydrogenation of diolefinic by-products from the dehydrogenation zone. The teachings of U.S. Pat. No. 5,276,231 are incorporated herein by reference.

U.S. Patent No. 5,196,574 (Kocal) and U.S. Pat. No. 5,344,997 (Kocal) describe alkylation of aromatics using a fluorided silica-alumina catalyst. U.S. Pat. No. 5,302,732 (Steigleder et al.) describes alkylation of aromatics using an ultra-low sodium silica-alumina catalyst. The teachings of U.S. Pat. Nos. 5,196,574, 5,302,732, and 5,344,997 are incorporated herein by reference.

PCT International Publication Nos. WO 00/23548 and WO 00/23549, which were published on Apr. 27, 2000, disclose processes for producing laundry detergents comprising modified alkylbenzene sulfonates and an alkylation step using two or more reactors. These publications state that operating a plurality of reactors allows for material with less preferred 2-methyl-2-phenyl index to be initially formed and to be converted into material with a more preferred 2-methyl-2-phenyl index.

U.S. Pat. No. 4,301,317 discloses reacting aromatic compounds with linear alkylating agents in the presence of mordenite.

U.S. Pat. No. 5,777,187 discloses a 2-step process for alkylation of benzene to form linear alkylbenzenes using a fluorine-containing mordenite catalyst and a fluorine containing clay catalyst, such as montmorillonite clay.

U.S. Pat. No. 6,090,993 discloses a process for preparing an aromatic solvent from a dioxane-contaminated aromatic stream by adsorption using molecular sieves or clay. The process relates to the production of benzene having a dioxane content less than 1 ppm, which is useful in the Detal process for producing linear alkyl benzene.

PCT International Publication No. WO 00/23404, which was published on Apr. 27, 2000, discloses a process for producing linear alkylbenzene by combining product from a fluorine-containing mordenite catalyst with the feed to a conventional linear alkylbenzene catalyst, such as hydrogen fluoride.

PCT International Publication No. WO 00/23405, which was published on Apr. 27, 2000, discloses a process for producing linear alkylbenzene having a high 2-phenyl isomer content by use of a fluorine-containing mordenite in conjunction with a conventional solid linear alkylbenzene alkylation catalyst, such as silica-alumina (with or without fluorine treatment), clay and aluminum chloride.

The use of mordenite to alkylate benzene with olefins to produce linear alkylbenzenes is described in the articles written by P. Meriaudeau et al., published in Catalysis Today 38 (1997) 243–247, by S. Sivasanker et al., published in Journal of Catalysis 138, 386–390 (1992), and by S. Sivasanker et al., published in New Frontiers in Catalysis, L. Guzci et al. (editors), Proceedings of the $10^{th}$ International Congress on Catalysis, Jul. 19–24, 1992, Budapest, Hungary, Elsevier Science Publishers B.V. 1993.

DETAILED DESCRIPTION OF THE INVENTION

Two feedstocks consumed in the subject process are an olefinic feedstock comprising an olefinic compound and an aromatic feedstock comprising an aryl compound.

The olefinic feedstock is typically a mixture of unreacted paraffins, linear (unbranched) olefins, and branched monoolefins. While the branched monoolefins may comprise a highly branched monoolefin, for the production of MAB, the branched monoolefin is preferably a lightly branched monoolefin. A lightly branched monoolefin, as used herein, refers to a monoolefin having a total number of carbon atoms of from about 8 to about 28, of which three or four of the carbon atoms are primary carbon atoms and none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Preferably, the lightly branched monoolefin has a total number of from 8 to 15 carbon atoms, and more preferably from 10 to 15 carbon atoms.

The lightly branched monoolefin generally comprises an aliphatic alkene having the general formula of $(p_i\text{-alkyl}_i)_i$- q-alkene. The lightly branched monoolefin consists of an aliphatic alkenyl chain, which is referred to by "alkene" in the $(p_i\text{-alkyl}_i)_i$-q-alkene formula, and is the longest straight chain containing the carbon-carbon double bond of the lightly branched monoolefin. The lightly branched monoolefin also consists of one or more alkyl group branches, each of which is attached to the aliphatic alkenyl chain and is designated by a corresponding "$(p_i\text{-alkyl}_i)_i$" in the $(p_i\text{-alkyl}_i)_i$-q-alkene formula. If it is possible to select two or more chains of equal lengths as the aliphatic alkenyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkenyl chain. The double bond is between carbon number q and carbon number (q+1) of the aliphatic alkenyl chain. The aliphatic alkenyl chain is numbered from one end to the other, the direction being chosen so as to give the lowest number possible to the carbon atoms bearing the double bond.

The lightly branched monoolefin may be an alpha monoolefin or a vinylidene monoolefin, but is preferably an internal monoolefin. As used herein, the term "alpha olefins" refers to olefins having the chemical formula, R—CH=CH$_2$. The term "internal olefins," as used herein, includes di-substituted internal olefins having the chemical formula R—CH=CH—R; tri-substituted internal olefins having the chemical formula R—C(R)=CH—R; and tetra-substituted olefins having the chemical formula R—C(R)=C(R)—R. The di-substituted internal olefins include beta internal olefins having the chemical formula R—CH=CH—CH$_3$. As used herein, the term "vinylidene olefins" refers to olefins having the chemical formula R—C(R)=CH$_2$. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond. Suitable lightly branched monoolefins include octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, and octacosenes.

For lightly branched monoolefins other than vinylidene olefins, the alkyl group branch or branches of the lightly branched monoolefin are generally selected from methyl, ethyl, and propyl groups, with shorter and normal branches being preferred. By contrast, for lightly branched monoolefins that are vinylidene olefins, the alkyl group branch attached to carbon number 2 of the aliphatic alkenyl chain may be selected not only from methyl, ethyl, and propyl groups but also from alkyl groups up to and including tetradecyl (C$_{14}$) groups, while any other alkyl group branch(es) of the vinylidene olefin is (are) generally selected from methyl, ethyl, and propyl groups with shorter and normal branches being preferred. For all lightly branched monoolefins, preferably the lightly branched monoolefin has only one alkyl group branch, but two alkyl group branches are also possible. Lightly branched monoolefins having either two alkyl group branches or four primary carbon atoms comprise generally less than 40 mol-%, and preferably less than about 30 mol-%, of the total lightly branched monoolefins, with the remainder of the lightly branched monoolefins having one alkyl group branch. Lightly branched monoolefins having either one alkyl group branch or three primary carbon atoms comprise preferably more than 70 mol-% of the total lightly branched monoolefins. Lightly branched monoolefins having only one alkyl group branch and where the sole alkyl group branch is a methyl group are referred to herein as monomethyl-alkenes and are a preferred component of the olefinic feedstock. Except for the alkyl group branch attached to carbon number 1 of the aliphatic alkenyl chain in a vinylidene olefin, any alkyl group branch can be bonded to any carbon on the aliphatic alkenyl chain.

Although vinylidene monoolefins may be present in the olefinic feedstock, they are normally a minor component and have a concentration of usually less than 0.5 mol-%, and more commonly less than 0.1 mol-%, of the olefins in the olefinic feedstock. Therefore, in the description that follows hereinafter, all references to the lightly branched monoolefins in general and to the olefinic feedstock in particular will assume that no vinylidene monoolefins are present.

In addition to the lightly branched monoolefin, other acyclic compounds may be in the olefinic feedstock. The olefinic feedstock may contain nonbranched (linear) olefins and monoolefins. Nonbranched (linear) olefins which may be in the olefinic feedstock have a total number of carbon atoms per paraffin molecule of generally from about 8 to about 28, preferably from 8 to 15, and more preferably from 10 to 14 carbon atoms. Two carbon atoms per nonbranched olefin molecule are primary carbon atoms and the remaining carbon atoms are secondary carbon atoms. A secondary carbon atom is a carbon atom which, although possibly bonded also to other atoms besides carbon, is bonded to only two carbon atoms. The nonbranched olefin may be an alpha monoolefin but is preferably an internal monoolefin. To the extent allowed by the definition of the term "internal olefin", when the nonbranched monoolefin is an internal monoolefin, any two carbon atoms of the aliphatic alkenyl chain may bear the double bond. When present in the olefinic feedstock with the lightly branched monoolefins, the linear olefin content may be as high as, or no more than, about 75 mol-% of the total monoolefins in the olefinic feedstock, but is generally less than about 40 mol-%, and may often be as low as 25 mol-%, of the total monoolefins in the olefinic feedstock. Because of the possible presence in the olefinic feedstock of linear monoolefins, in addition to the lightly branched monoolefins, the bulk olefinic feedstock may contain, on average, fewer than 3, or between 3 and 4, primary carbon atoms per monoolefin molecule in the olefinic feedstock. Depending on the relative proportions of linear and lightly branched monoolefins, the olefinic feedstock may have from 2.25 to 4 primary carbon atoms per monoolefin molecule.

Other acyclic compounds in the olefinic feedstock include paraffins having the same number of carbon atoms as the lightly branched monoolefins. Linear and/or nonlinear paraffins in the olefinic feedstock have a total number of carbon atoms per paraffin molecule of generally from about 8 to about 28, preferably from 8 to 15, and more preferably from 10 to 14 carbon atoms. The nonlinear paraffins in the olefinic feedstock may include lightly branched paraffins and may also include paraffins having at least one quaternary carbon atom. Such linear and nonlinear paraffins are expected to act as a diluent and to not materially interfere with alkylation and other reactions that take place in the process of the present invention. However, the presence of such diluents generally results in higher volumetric flow rates of process streams, and, in order to accommodate these higher flow rates, larger equipment in the first and second reaction zones (i.e., larger reactors and more alkylation catalyst), and larger product recovery facilities may be required.

Monoolefins that are more highly branched than the lightly branched monoolefins may also be present in the olefinic feedstock, but preferably their concentration in the olefinic feedstock is minimized because on alkylation such highly branched monoolefins tend to form BAB. For example, if the olefinic feedstock contains monoolefin molecules consisting of at least one quaternary carbon atom, phenyl-alkanes that have in the aliphatic alkyl portion a quaternary carbon atom that is not bonded by a carbon-carbon bond with a carbon atom of the aryl portion tend to form. Therefore, monoolefin molecules consisting of at least one quaternary carbon atom generally comprise less than 10 mol-%, preferably less than 5 mol-%, more preferably less than 2 mol-%, and most preferably less than 1 mol-% of the olefinic feedstock.

The production of the olefinic feedstock is not an essential element of this invention, and any suitable method for producing the olefinic feedstock may be used. One method for the production of the olefinic feedstock consists of three steps. First, nonbranched (linear) paraffinic hydrocarbons are separated from a kerosene boiling range petroleum fraction using a process such as the UOP Molex™ process, a commercially proven method for the liquid-phase adsorption separation of normal paraffins from isoparaffins and cycloparaffins using the UOP Sorbex separation technology. See Chapters 10.3 and 10.7 in the book entitled *Handbook of Petroleum Refining Process*, Second Edition, edited by Robert A. Meyers, published by McGraw-Hill, New York, 1997. Second, the paraffinic hydrocarbons are passed to a skeletal isomerization zone, which decreases the linearity and adjusts the number of primary carbon atoms of the paraffinic hydrocarbons. In the skeletal isomerization zone, the paraffins and hydrogen contact a catalyst comprising a metal of Group VIII (IUPAC 8–10) of the Periodic Table and a support material, such as those exemplified by U.S. Pat. Nos. 4,310,440; 4,440,871; 4,793,984; 4,758,419; 4,943,424; 5,087,347; 5,158,665; 5,208,005; 5,246,566; 5,716,897; and 5,851,949. The effluent from contacting the catalyst is partially condensed and separated to produce isomerized paraffinic hydrocarbons. Third, the isomerized paraffinic hydrocarbons pass to a dehydrogenation zone, which converts the isomerized paraffinic hydrocarbons to isomerized monoolefinic hydrocarbons. The isomerized paraffins contact a catalyst, such as those exemplified by U.S. Pat. Nos. 3,274,287; 3,315,007; 3,315,008; 3,745,112; 4,430,517; 4,716,143; 4,762,960; 4,786,625; and 4,827,072. After contacting the catalyst, the effluent is partially condensed, separated from by-product hydrogen, and further separated to produce isomerized monoolefinic hydrocarbons, which can form the olefinic feedstock. If, however, the isomerized monoolefinic hydrocarbons contain diolefins, which are a common by-product of the dehydrogenation step, selective diolefin hydrogenation to convert the diolefins to monoolefins may be used, such as described in U.S. Pat. No. 5,276,231. The olefinic feedstock has a concentration of diolefins of preferably less than 0.3 wt-%. If the isomerized monoolefinic hydrocarbons contain aromatics, such as those aromatics formed as by-products in some dehydrogenation processes, selective removal of aromatics, which is also described in U.S. Pat. No. 5,276,231, may be used. The olefinic feedstock has a concentration of aromatics of preferably less than 1.0 wt-%.

The composition of a mixture of lightly branched monoolefins can be determined by analytical methods that are well-known to a person of ordinary skill in the art of gas chromatography and need not be described here in detail. The article written by H. Schulz, et al. and published starting at page 315 of the Chromatographia 1, 1968, which is incorporated herein by reference, describes a temperature-programmed gas chromatograph apparatus and method that is suitable for identifying components in complex mixtures of paraffins. A person of ordinary skill in the art can modify the apparatus and method in the article in the article by Schulz et al. to equip the injector with a hydrogenator insert tube in order to hydrogenate the lightly branched monoolefins to lightly branched paraffins in the injector. The lightly branched paraffins are then separated and identified using essentially the apparatus and method described in the article by Schulz et al.

The aromatic feedstock comprises an aryl compound, which is benzene when the process is detergent alkylation. In a more general case, the aryl compound of the aromatic feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

In accord with this invention, two reaction zones are employed for reacting the olefinic feedstock comprising the lightly branched monoolefins with the aromatic feedstock comprising the aryl compound.

The first reaction zone contains one or more reactors containing the first catalyst. The feed to the respective reactors of the first reaction zone may contact the respective catalysts in either upflow, downflow, or radial-flow mode. Reactions in the first reaction zone may be conducted either as a batch method or in a continuous manner, although the latter is greatly preferred. The respective catalysts in each of the respective reactors of the first reaction zone may be in a packed bed, a moving bed, or a fluidized bed. The aromatic feedstock or the olefinic feedstock may pass to each respective reactor of the first reaction zone either separately or in an admixture with the other feedstock, or in an admixture with effluent from another reactor of the first reaction zone. The aromatic feedstock may contact the respective catalyst in each of the respective reactors of the first reaction zone in either upflow, downflow, or radial-flow mode. Likewise, the olefinic feedstock to each respective reactor of the first reaction zone may be passed either upflow or downflow, or horizontally as in a radial bed reactor.

The reaction of the aryl compound with the olefinic compound, preferably with the lightly branched monoolefins, in the first reaction zone produces $(m_i$-alkyl$_i)$-$_i$-n-phenyl-alkanes, where the aliphatic alkyl group has two, three, or four primary carbon atoms per phenyl-alkane molecule. Preferably, the aliphatic alkyl group has three primary carbon atoms per phenyl-alkane molecule, and more preferably one of the three primary carbon atoms is in a methyl group at one end of the aliphatic alkyl chain, the second primary carbon atom is in a methyl group at the other end of the chain, and the third primary carbon atom is in a single methyl group branch attached to the chain. However, it is not necessary that all of the $(m_i$-alkyl$_i)$-$_i$-n-phenyl-alkanes produced by the present invention have the same number of primary carbon atoms per phenyl-alkane molecule. Generally from about 0 mol-% to about 75 mol-%, and preferably from about 0 mol-% to about 40 mol-%, of the $(m_i$-alkyl$_i)$-$_i$-n-phenyl-alkanes produced may have 2 primary carbon atoms per phenyl-alkane molecule. Generally, as many as possible, and typically from about 25 mol-% to about 100 mol-%, of the $(m_i$-alkyl$_i)$-$_i$-n-phenyl-alkanes produced may have 3 primary carbon atoms per phenyl-alkane molecule. Generally from about 0 mol-% to about 40 mol-% of the $(m_i\text{-alkyl}_i)_i$-n-phenyl-alkanes produced may have 4 primary carbon atoms. Thus, (m-methyl)-n-phenyl-alkanes having only one methyl group branch are preferred and are referred to herein as monomethyl-phenyl-alkanes. It is expected that the number of primary, secondary, and tertiary carbon atoms per product phenyl-alkane molecule can be determined by high resolution multipulse nuclear magnetic resonance (NMR) spectrum editing and distortionless enhancement by polarization transfer (DEPT), which is described in the brochure entitled "High Resolution Multipulse NMR Spectrum Editing and DEPT," which is distributed by Bruker Instruments, Inc., Manning Park, Billerica, Mass., USA, and which is incorporated herein by reference.

The alkylation of the aryl compound with the lightly branched monoolefins has a selectivity to nonquaternary 2-phenyl-alkanes of generally from about 40 to about 100 and preferably from about 60 to about 100, and an end quaternary phenyl-alkane selectivity of generally less than 10. Quaternary phenyl-alkanes can form by alkylating the aryl compound with a lightly branched monoolefin having at least one tertiary carbon atom. A tertiary carbon atom is a carbon atom which, while also possibly bonded to other atoms besides carbon, is bonded to only three carbon atoms. If, on alkylation, a tertiary carbon atom of the monoolefin forms a carbon-carbon bond with one of the carbon atoms of the aryl compound, that tertiary carbon atom becomes a quaternary carbon atom of the aliphatic alkyl chain. Depending on the location of the quaternary carbon atom with respect to the ends of the aliphatic alkyl chain, the resulting quaternary phenyl-alkane may be either an internal or an end quat.

While the reaction conditions of the first reaction zone are sufficient to alkylate the aryl compound with the lightly branched monoolefin, it is believed that under these reaction conditions only minimal skeletal isomerization of the lightly branched monoolefin occurs. As used herein, skeletal isomerization of an olefin means isomerization which changes the number of carbon atoms in the aliphatic alkenyl chain of the olefin or in the aliphatic alkyl chain of a phenyl-alkane. By minimal skeletal isomerization it is meant that generally less than 25 mol-%, and preferably less than 10 mol-%, of the olefin or the aliphatic alkyl chain undergoes skeletal isomerization. It is further believed that under the reaction conditions in the first reaction zone minimal skeletal isomerization occurs for any other olefins in the olefinic feedstock. Thus, alkylation preferably occurs in the substantial absence of skeletal isomerization of the lightly branched monoolefin, and the extent of light branching of the lightly branched monoolefin is identical to the extent of light branching in the aliphatic alkyl chain in the phenyl-alkane product molecule. Accordingly, the number of primary carbon atoms in the lightly branched monoolefin is preferably the same as the number of primary carbon atoms per phenyl-alkane molecule. Insofar as an additional methyl group branch does form on the aliphatic alkyl chain of the phenyl-alkane product, the number of primary carbon atoms in the phenyl-alkane product may be slightly higher the number of primary carbon atoms in the lightly branched monoolefin. Finally, although the formation of 1-phenyl-alkane product is not significant at alkylation conditions, insofar as a 1-phenyl-alkane molecule is formed by alkylating an aryl compound with a lightly branched monoolefin having a primary carbon atom on each end of the aliphatic alkenyl chain, the number of primary carbon atoms in the phenyl-alkane product will be slightly less than the number of primary carbon atoms in the lightly branched monoolefin.

Although the stoichiometry of the reaction in the first reaction zone requires only 1 molar proportion of aryl compound per mole of total monoolefins, the use of a 1:1 mole proportion results in excessive olefin polymerization and can result in polyalkylation. On the other hand, it is desired to have the aryl compound:monoolefin molar ratio as close to 1:1 as possible to maximize utilization of the aryl compound and to minimize the recycle of unreacted aryl compound. The actual molar proportion of aryl compound to total monoolefin will therefore have an important effect on both conversion of the olefinic compound and, perhaps more importantly, selectivity of the alkylation reaction in the first reaction zone. In order to carry out alkylation with the conversion and selectivity required using the catalysts of this invention's process, the total aryl compound: monoolefin molar ratio may be generally from about 1:1 up to about 50:1, more commonly from about 2.5:1 up to about 50:1, and normally from about 8:1 to about 35:1. In a preferred embodiment, the olefinic feedstock may be fed into several discrete points within each respective reactor of the first reaction zone, and at each point the aryl compound:monoolefin molar ratio may be greater than 50:1. However, the total aryl compound:monoolefin ratio used in this preferred embodiment of this invention still will be within the stated range.

The reaction conditions of the first reaction zone include a temperature in the range between about 176° F. (80° C.) and about 392° F. (200° C.), most usually at a temperature not exceeding 347° F. (175° C.). Since the alkylation is conducted in at least partial liquid phase, and preferably in either an all-liquid phase or at supercritical conditions, pressures must be sufficient to maintain reactants in the liquid phase. The requisite pressure necessarily depends upon the olefin, the aryl compound, and temperature, but normally is in the range of 200–1000 psi(g) (1379–6895 kPa(g)), and most usually 300–500 psi(g) (2069–3448 kPa (g)). The total feed mixture, that is, aromatic feedstock plus olefinic feedstock, passes through the first reaction zone at a liquid hourly space velocity (LHSV) between about 0.3 and about 6 $hr^{-1}$ depending upon the alkylation temperature, how long the catalyst has been used, and so on. Lower values of LHSV within this range are preferred. As used herein, the abbreviation 'LHSV' means liquid hourly space velocity, which is defined as the volumetric flow rate of liquid per hour divided by the catalyst volume, where the liquid volume and the catalyst volume are in the same volumetric units. The conversion of the olefinic compound in the first reaction zone is generally greater than 90%, and preferably greater than 95%. Olefin conversion in a reaction zone is computed by subtracting the moles of the olefinic compound withdrawn from a reaction zone from the moles of the olefinic compound introduced into the reaction zone, dividing that difference by the moles of the olefinic compound introduced into the reaction zone, and multiplying that quotient by 100.

The catalyst in the first reaction zone, referred to herein as the first catalyst, comprises a zeolite having a MOR zeolite structure type. Such zeolites include mordenite. This zeolite structure type, the term "zeolite structure type," and the term "isotypic framework structure" are used herein as they are defined and used in the *Atlas of Zeolite Structure Types*, by W. M. Meier, et al., published on behalf of the Structure Commission of the International Zeolite Association by Elsevier, Boston, Mass., USA, Fourth Revised Edition, 1996.

Useful zeolites for the first catalyst in the present invention generally have at least 10 percent of the cationic sites thereof occupied by ions other than alkali or alkaline-earth metals. Such other ions include, but are not limited to hydrogen, ammonium, aluminum, rare earth, zinc, copper, and aluminum. Of this group, particular preference is accorded ammonium, hydrogen, rare earth, or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, such as the metals of Groups IIIB (IUPAC 3), IVB (IUPAC 4), VIB (IUPAC 6), VIIB (IUPAC 7), VIII (IUPAC 8–10), and IIB (IUPAC 12). It is also contemplated that the zeolites may, in some instances, desirably be subjected to thermal treatment, including steaming or calcination in air, hydrogen, or an inert gas, e.g. nitrogen or helium. A suitable steaming treatment comprises contacting the zeolite with an atmosphere containing from about 5 to about 100% steam at a temperature of from about 250° C. (482° F.) to 1000° C. (1832° F.). Steaming may last for a period of between about 0.25 and about 100 hours and may be conducted at pressures ranging from sub-atmospheric to several hundred atmospheres.

It may be useful to incorporate the zeolites that are useful in this invention in another material, e.g., a matrix material or binder that is resistant to the temperature and other conditions used in the process. Suitable matrix materials include synthetic substances, naturally occurring substances, and inorganic materials such as clay, silica, and/or metal oxides. Matrix materials can be in the form of gels including mixtures of silica and metal oxides. Gels including mixtures of silica and metal oxides may be either naturally occurring or in the form of gels or gelatinous precipitates. Naturally occurring clays which can be composited with the zeolite used in this invention include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used as a matrix material in their raw states as originally mined, or can be subjected to calcination, acid treatment or chemical modification prior to their use as matrix materials. In addition to the foregoing materials, the zeolite used in this invention may be compounded with a porous matrix material, such as alumina, silica-alumina, silica-magnesia, silica-zirconia, silica-thoria, silica-beryllia, silica-titania, and aluminum phosphate as well as ternary combinations, such as silica-alumina-thoria, silica-alumina-zirconia, silica-alumina-magnesia, and silica-magnesia-zirconia. The matrix material may be in the form of a cogel. The relative proportions of and matrix material may vary widely, with the zeolite content ranging generally from between about 1 and about 99% by weight, usually in the range of about 5 to about 80% by weight, and preferably in the range of about 30 to about 80% by weight, of the combined weight of zeolite and matrix material.

The zeolites that are useful in the alkylation catalyst generally have a framework silica:alumina molar ratio of from about 5:1 to about 100:1. When the zeolite of the alkylation catalyst is mordenite, the mordenite has a framework silica:alumina molar ratio generally of from about 12:1 to about 90:1, and preferably of from about 12:1 to about 25:1. As used herein, the term "framework silica:alumina molar ratio" means the molar ratio of silica per alumina, that is the molar ratio of $SiO_2$ per $Al_2O_3$, in the zeolite framework.

When zeolites have been prepared in the presence of organic cations they may not be sufficiently catalytically active for alkylation. Without being bound to any particular theory, it is believed that the insufficient catalytic activity is the result of the organic cations from the forming solution occupying the intracrystalline free space. Such catalysts may be activated, for example, by heating in an inert atmosphere at 540° C. (1004° F.) for one hour, ion exchanging with ammonium salts, and calcining at 540° C. (1004° F.) or above in air. Preferably, the calcination conditions are sufficient to decompose at least a portion of, and more preferably all of, any ammonia present in the catalyst. The presence of organic cations in the forming solution may be essential to forming particular zeolites. Some natural zeolites may sometimes be converted to zeolites of the desired type by various activation procedures and other treatments such as ion exchange, steaming, alumina extraction, and calcination. When synthesized in the alkali metal form, the zeolite is conveniently converted to the hydrogen form, generally by intermediate formation of the ammonium form as a result of ammonium ion exchange and calcination of the ammonium form to yield the hydrogen form. Although the hydrogen form of the zeolite catalyzes the reaction successfully, the zeolite may also be partly in the alkali metal form.

The first reaction zone produces a first effluent comprising the desired phenyl-alkanes. In addition to phenyl-alkanes, the first effluent may also comprise paraffinic hydrocarbons, lightly branched monoolefinic hydrocarbons, other acyclic hydrocarbons, and polyalkylbenzenes such as phenyl-dialkanes and phenyl-trialkanes. While the production of quaternary 2-phenyl-alkanes and end quaternary phenyl-alkanes in the first reaction zone are preferably minimized, nevertheless some production of each of these usually occur and thus each is often present to some extent in the first effluent. It is an objective of this invention, however, to provide a process with an increased selectivity to nonquaternary 2-phenyl-alkanes and a decreased selectivity to end quaternary phenyl-alkanes. In accord with this invention, the effluent of the first reaction zone passes to a second reaction zone.

The second reaction zone contains one or more reactors containing the second catalyst. The feed to the respective reactors may contact the respective catalysts in either upflow, downflow, or radial-flow mode. Reactions in the second reaction zone may be conducted either as a batch method or in a continuous manner, although the latter is greatly preferred. The respective catalysts in each of the respective reactors may be in a packed bed, a moving bed, or a fluidized bed. The first effluent may be passed to each respective reactor either separately or in an admixture with the aromatic feedstock, the olefinic feedstock, or both. However, it is not a requirement of this invention that any aromatic feedstock or any olefinic feedstock be passed to the second reaction zone. But if either any aromatic feedstock or any olefinic feedstock passes to any reactor in the second reaction zone, that feedstock may be introduced in either upflow, downflow, or radial-flow mode, and/or may be introduced in an admixture with the other feedstock. If the olefinic feedstock is introduced to any reactor in the second reaction zone, the olefinic feedstock is introduced at a total aryl compound:monoolefin molar ratio of generally from about 1:1 up to about 50:1, and more commonly between 2.5:1 and 50:1, and if fed into several discrete points within the second reaction zone, at each point the aryl compound-:monoolefin molar ratio may be greater than 50:1.

The second catalyst is a solid catalyst having an acid function, that is a solid acid catalyst. Suitable second catalysts include materials comprising amorphous silica-alumina. A fluorided silica-alumina catalyst, particularly one with a weight ratio of silica to alumina in the range of at least 0.5:1 (33 wt-%) up to as high as 9:1 (90 wt-%) containing from 1 to 6 wt-% fluoride, is particular effectively effective as the second catalyst. See U.S. Pat. Nos. 5,196,574 and 5,344,997, the teachings of which are incorporated herein by reference. The stated silica-alumina weight ratio is a useful compromise between selectivity and activity. Selectivity of processes using the fluorided silica-aluminas of this preferred catalyst increases with increasing silica content, which recommends or suggests the use of as high a silica level as possible. However, the activity of the fluorided materials increases initially, appears to pass through a maximum at about a 3:1 ratio of silica:alumina, and then decreases thereafter. Accordingly, although fluorided silica-aluminas can be used throughout the given range, those having a silica to alumina weight ratio between about 65:35 and 85:15 are preferred for this catalyst. Preferably, this preferred fluorided silica-alumina catalyst contains from about 1 up to 6 weight percent fluoride based on volatile-free finished silica-alumina catalyst. Higher fluoride levels may be used but without any substantial incremental benefit. The preferred fluoride level depends on the silica-alumina ratio. For example, for a 75:25 silica:alumina ratio fluoride levels between about 1.5 and 3.5 are preferred. The second catalysts include silica-aluminas having an ultra-low sodium content of preferably less than about 0.5 weight percent and more preferably less than about 0.1 weight percent. See U.S. Pat. No. 5,302,732, the teachings of which are incorporated herein by reference. The silica-aluminas may contain a weight ratio of silica to alumina of at least 1:1 up to as high as 19:1, but a silica:alumina ratio of 2:1 (67:33) up to about 19:1 (ca. 95:5) is preferred.

The effluent of the second reaction zone contains the same kinds of ($m_i$-alkyl$_j$)$_i$-n-phenyl-alkanes described previously as having been produced in the first reaction zone. The effluent of the second reaction zone contains one or more phenyl-alkanes having one aryl portion and one aliphatic alkyl portion containing from about 8 to about 28 carbon atoms and preferably from about 10 to about 15 carbon atoms and having 2, 3, or 4 primary carbon atoms and no quaternary carbon atoms except for any quaternary carbon atom bonded by a carbon-carbon bond with a carbon atom of the aryl portion. In addition, the effluent of the second reaction zone has a reduced content of nonquaternary 2-phenyl-alkanes and/or and quaternary phenyl-alkanes relative to the effluent of the first reaction zone. Based on the effluent of the second reaction zone, the process has a selectivity to nonquaternary 2-phenyl-alkanes of generally from about 40 to about 100 and preferably from about 60 to about 100, and an end quaternary phenyl-alkane selectivity of generally less than 10.

Where the process of this invention has an intermediate selectivity to nonquaternary 2-phenyl-alkanes (denoted $N_i$) based on the effluent of the first reaction zone, an intermediate selectivity to end quaternary phenyl-alkanes (denoted $E_i$) based on the effluent of the first reaction zone, an overall selectivity to nonquaternary 2-phenyl-alkanes (denoted $N_o$) based on the effluent of the second reaction zone, and an overall selectivity to end quaternary phenyl-alkanes (denoted $E_o$) based on the effluent of the second reaction zone, the quotient $(E_i-E_o)/(E_i)$ is preferably greater than the quotient $(N_i-N_o)/(N_i)$. Also, $E_o$ is preferably less than $E_i$.

Without limiting the invention as set forth in the claims to any particular theory, it is believed that the reaction conditions of the second reaction zone are sufficient so that some skeletal isomerization of phenyl-alkanes, in particular of nonquaternary 2-phenyl-alkanes and of end quaternary phenyl-alkanes, occurs. Examples of possible reactions that may skeletally isomerize these phenyl-alkanes include detachment of the aliphatic alkyl group from the phenyl group followed by reattachment of the aliphatic alkyl group, shift of one or more alkyl branches along the aliphatic alkyl chain of the aliphatic alkyl group, and shift of the phenyl group along the aliphatic alkyl chain. It is believed that a net change in the number of alkyl group branches on the aliphatic alkyl chain of the phenyl-alkane product need not necessarily occur in the second reaction zone. In addition or alternatively, it is believed that some cracking of end quaternary phenyl-alkanes may occur in the second reaction zone, and some nonquaternary 2-phenyl-alkanes may crack as well. It is also believed that the reaction conditions in the second reaction zone may preferentially crack end quaternary phenyl-alkanes over nonquaternary 2-phenyl-alkanes. This may explain why use of the second reaction zone in this invention can shift the distribution of detergent-range phenyl-alkanes toward nonquaternary 2-phenyl-alkanes and away from quaternary phenyl-alkanes. While a process that uses only a catalyst comprising mordenite and that operates at a relatively high alkylation temperature can achieve a relatively low overall selectivity to end quaternary phenyl-alkanes that is comparable to the process of this invention, such a process does so with much more cracking than the process of this invention.

The reaction conditions of the second reaction zone include a temperature in the range between about 176° F. (80° C.) and about 437° F. (225° C.), usually between about 347° F. (175° C.) and about 437° F. (225° C.), and most usually at a temperature not exceeding 392° F. (200° C.). Since the reaction is conducted in at least partial liquid phase, and preferably in either an all-liquid phase or at supercritical conditions, pressures for must be sufficient to maintain reactants in the liquid phase. The requisite pressure necessarily depends upon the olefin (if any), the aryl compound (if any), the phenyl-alkanes, and temperature, but normally is in the range of 200–1000 psi(g) (1379–6895 kPa(g)), and most usually 300–500 psi(g) (2069–3448 kPa (g)). The total feed mixture, that is, effluent of the first reaction zone plus any aromatic feedstock as well as any olefinic feedstock, passes through the second reaction zone at a liquid hourly space velocity (LHSV) between about 0.3 and about 12 $hr^{-1}$ depending upon the alkylation temperature, how long the catalyst has been used, and so on. Higher values of LHSV within this range are preferred.

The second reaction zone produces a second effluent that enters separation facilities for the recovery of products and recyclable feed compounds. The second effluent stream passes into a column (commonly called a "benzene column," when the aryl compound comprises benzene) which produces an overhead stream containing the aryl compound and a bottoms stream containing the phenyl-alkane product. This bottoms stream passes into a paraffin column which produces an overhead liquid stream containing unreacted paraffins and a bottoms stream containing the product phenyl-alkanes and any higher molecular weight side product hydrocarbons formed in the first or second reaction zones. This paraffin column bottoms stream may pass to a rerun column which produces an overhead alkylate product stream containing the detergent-grade phenyl-alkanes and a rerun column bottoms stream containing polymerized olefins and polyalkylated benzenes (heavy alkylate). Alternatively, if the heavy alkylate content of the paraffin column bottoms stream is sufficiently low, a rerun column is not necessary and the paraffin column bottoms stream may be recovered as the net detergent phenyl-alkanes stream from the process.

It is within the scope of the present invention to recycle an aliquot portion of the effluent of the first reaction zone to the first reaction zone, to recycle an aliquot portion of the effluent of the second reaction zone to the first reaction zone, to recycle an aliquot portion of the effluent of the second reaction zone to the second reaction zone, and to recover phenyl-alkane from the process from an aliquot portion of the effluent of the first reaction zone. Each of these may be done alone or in combination with one or more of the others. An aliquot portion of an effluent is a portion that has essentially the same composition as the effluent.

The first catalyst preferably represents about 20% to about 99% by volume of the total catalyst in the present process. The relative volumes of first and second catalyst depend on product objectives as well as whether the process incorporates previously utilized equipment. If the product objective of an all-new process unit is maximum practical production of phenyl-alkanes, the first catalyst advantageously comprises a substantial proportion, preferably about 10% to about 60%, of the total catalyst. If a second reaction zone is added to an existing first reaction zone, on the other hand, the second reforming catalyst optimally comprises a relatively small proportion of the total catalyst in order to minimize the impact of the new reaction zone on the existing process. In the latter case, preferably about 55% to about 95% of the total catalyst volume of the process is represented by the first catalyst.

Either the first or second catalyst used in the present invention may become deactivated by by-products which are preferentially adsorbed by the catalysts. Such by-products include, for example, polynuclear hydrocarbons in the 10 to 20 carbon atom range formed in the dehydrogenation of $C_6$ to $C_{20}$ linear paraffins and also include products of higher molecular weight than the desired monoalkyl benzenes, e.g., di- and tri-alkyl benzenes, as well as olefin oligomers. Although it can be readily appreciated that such catalyst deactivating agents or "poisons" are an adjunct of aromatic alkylation, fortunately it has been observed that such deactivating agents can be readily desorbed from the first and second catalysts by washing the catalyst with the aromatic feedstock. In particular, the preferred mordenite, silica-alumina, and fluorided silica-alumina catalysts for use in this invention can be reactivated in this manner. Thus, catalyst reactivation, or catalyst regeneration as the term is more commonly employed, is conveniently effected by flushing the catalyst with the aryl compound to remove accumulated poisons from the catalyst surface, generally with restoration of 100% of catalyst activity.

The first or second catalyst may be contained in a fixed-bed reactor, or in a moving-bed reactor or in a fluidized bed reactor whereby catalyst may be continuously withdrawn and added. These alternatives are associated with catalyst regeneration options known to those of ordinary skill in the art, such as: (1) a semiregenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst becomes deactivated and the catalyst in isolated reactor is regenerated and reactivated while the other reactors remain on-stream; (3) continuous regeneration of catalyst withdrawn from a moving-bed reactor or a fluidized bed reactor, with reactivation and substitution with the reactivated catalyst; or (4) a hybrid system with semiregenerative and continuous-regeneration provisions in the same zone. The preferred embodiment of the present invention is the fixed-bed reactor in a swing-reactor first reaction zone and a fixed-bed reactor in a swing-reactor second reaction zone.

Each of the first and second reaction zone may comprise a single reactor containing the respective catalyst or, alternatively, two or more parallel reactors with valving as known in the art to permit alternative cyclic regeneration. The choice between a single reactor and parallel cyclical reactors depends inter alia on the reactor volume and the need to maintain a high degree of yield consistency without interruption; preferably, in any case, the reactors of each zone are valved for removal from the process combination so that the respective catalyst may be regenerated or replaced while the other reactor(s) of the zone remain in operation.

In an alternative embodiment, it is within the ambit of the invention that each of the two zones, and in particular the first reaction zone, comprises two or more reactors with intercooling between reactors to lower the temperature and maintain alkylation conditions. This may be advantageous, especially in the first reaction zone, since the major reaction occurring in the first reaction zone is the alkylation of the aryl compound with the olefinic compound, and the resulting exothermic heat of reaction may heat the feedstocks above the temperature at which alkylation takes place in the substantial absence of skeletal isomerization. This is less advantageous in the second reaction zone, where the principal reactions are believed to be less exothermic. In another alternative embodiment, reaction temperatures may be maintained in the first reaction zone by inclusion of heat-exchange internals in a reactor of the first reaction zone. The heat-exchange internals may bayonet-tubes or elongate compartments alternatively containing catalyst with reactants and a heat carrier fluid.

In a preferred embodiment of the process aspect of this invention, this invention is a process for producing a preferred MAB composition comprising arylalkanes (phenyl-alkanes) having one aryl group and one aliphatic alkyl group, wherein the arylalkanes have:

(i) an average weight of the aliphatic alkyl groups of the arylalkanes of between the weight of a $C_{10}$ aliphatic alkyl group and a $C_{13}$ aliphatic alkyl group;

(ii) a content of arylalkanes having the phenyl group attached to the 2- and/or 3-position of the aliphatic alkyl group of greater than 55 wt-% of the arylalkanes; and (iii) an average level of branching of the aliphatic alkyl groups of the arylalkanes of from 0.25 to 1.4 alkyl group branches per arylalkane molecule when the sum of the contents of 2-phenyl-alkanes and 3-phenyl-alkanes is more than 55 wt-% and less than or equal to 85 wt-% of the arylalkanes, or an average level of branching of the aliphatic alkyl groups of the arylalkanes of from 0.4 to 2.0 alkyl group branches per arylalkane molecule when the sum of the concentrations of 2-phenyl-alkanes and the 3-phenyl-alkanes is greater than 85 wt-% of the arylalkanes; and (iv) wherein the aliphatic alkyl groups of the arylalkanes comprise primarily linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise primarily small substituents, such as methyl group branches, ethyl group branches, or propyl group branches, and wherein the alkyl group branches if any attach to any position on the aliphatic alkyl chain of the aliphatic alkyl groups provided that arylalkanes having at least one quaternary carbon atom on the aliphatic alkyl group comprise less than 20% of the arylalkanes.

One process for producing this preferred MAB composition comprises using as the olefinic feedstock monoolefins having an average weight between the weight of a $C_{10}$ olefin and a $C_{13}$ olefin and an average level of branching of from 0.25 to 1.4, or of from 0.4 to 2.0, alkyl group branches per monoolefin molecule. These monoolefins primarily comprise linear monoolefins, mono-branched monoolefins, or di-branched monoolefins, and the alkyl group branches if any on the aliphatic alkyl chain of the monoolefins primarily comprise small substituents, such as methyl group branches, ethyl group branches, or propyl group branches. The alkyl group branches of the monoolefins may be attached to any position on the aliphatic alkyl chain of the monoolefin, subject to certain limitations that depend on the desired characteristics of the resultant arylalkanes. The monoolefins alkylate an aryl compound to produce arylalkanes. The resultant arylalkanes have the characteristics that the arylalkanes having the phenyl group attached to the 2- and/or 3-position of the aliphatic alkyl group comprise greater than 55 wt-% of the arylalkanes, and the arylalkanes having at least one quaternary carbon atom on the aliphatic alkyl group comprise less than 20% of the arylalkanes.

Sulfonation of the phenyl-alkanes produced by the processes of this invention can be accomplished by contacting the phenyl-alkane compounds with any of the well-known sulfonation systems, including those described in *Detergent Manufacture Including Zeolite Builders and Other New Materials*, by Marshall Sittig, Noyes Data Corporation, Park Ridge, N.J., 1979, and in Volume 56 of "Surfactant Science" series, Marcel Dekker, Inc., New York, N.Y., 1996. Sulfonation of the phenyl-alkane compounds produces a sulfonated product comprising phenyl-alkane sulfonic acids. Common sulfonation systems employ sulfonating agents such as sulfuric acid, chlorosulfonic acid, oleum, and sulfur trioxide. Sulfonation using a mixture of sulfur trioxide and air is described in U.S. Pat. No. 3,427,342.

After sulfonation, the sulfonated product can be neutralized by contact with any suitable alkali, such as sodium, potassium, ammonium, magnesium, calcium, and substituted ammonium alkalis, and mixtures thereof. Neutralization of the phenyl-alkane sulfonic acids produces a neutralized product comprising phenyl-alkane sulfonates. Suitable neutralizing agents include sodium hydroxide, potassium hydroxide, ammonium hydroxide, sodium carbonate, sodium bicarbonate, potassium carbonate, magnesium hydroxide, magnesium carbonate, basic magnesium carbonate (magnesia alba), calcium hydroxide, and calcium carbonate, and mixtures thereof.

In other aspects of the present invention, this invention is the MAB compositions and the MABS compositions produced by the processes disclosed herein.

In yet another aspect of the present invention, this invention is the use of the MAB compositions produced by the processes disclosed herein as lubricants. These phenyl-alkanes are believed to have properties of viscosity, temperature-dependence of viscosity, and density that make them advantageous for use as petroleum lubricants. The use of phenyl-alkanes as lubricants is described, for example, in the article by E. R. Booser in *Kirk-Othmer Encyclopedia of Chemical Technology*, Fourth Edition, Volume 15, John Wiley and Sons, New York, N.Y., USA, 1995, pp. 463–517, to which reference is made for a description of such lubricants and their use.

In still another aspect, this invention is the use of the MABS compositions produced by the processes disclosed herein as lubricant additives. It is believed that phenyl-alkane sulfonates, either in the form of normal salts or basic salts of phenyl-alkane sulfonic acids, produced as disclosed herein, have the ability to reduce or prevent deposits in engines operating at high temperatures. As used herein, the term "normal salt" of an acid means a salt which contains the stoichiometric amount of metal required for the neutralization of the acidic group or groups present, and the term "basic salt" means a salt which contains more metal than is required for the neutralization reaction. The excess metal in the form of basic salts is believed to be capable of neutralizing oil oxidation combustion products and "blow-by" fuel combustion products. Phenyl-alkane sulfonates and their use as lubricant additives, in particular as detergents, is described, for example, in the above-mentioned Booser article; in *Lubricant Additives*, by C. V. Smalheer and R. K. Smith, The Lezius-Hiles Co., Cleveland, Ohio, USA, 1967, pp. 2–3; and in the article by R. W. Watson and T. F. McDonnell, Jr., entitled "Additives—The Right Stuff for Automotive Engine Oils," in *Fuels and Lubricants Technology: An Overview SP*-603, Society of Automotive Engineers, Warrendale, Pa., USA, October 1984, pp. 17–28.

It is within the scope of the invention that the order of the first reaction zone and the second reaction zone is reversed, i.e., an alternative embodiment is reacting the aromatic feedstock and the olefinic feedstock with a silica-alumina catalyst to obtain a phenyl-alkane effluent which is processed in a reaction zone containing a mordenite catalyst to obtain a phenyl-alkane product. Operating conditions and catalysts for the two zones in this embodiment are within the parameters described above.

The following examples are solely for purposes of illustration. These examples show in detail how the invention claimed below may be effected, and are not meant to limit the scope of this invention to the embodiments shown in the examples. These examples are not meant to limit the scope of this invention as set forth in the claims.

EXAMPLE 1

Example 1 illustrates preparation of a mordenite-containing alkylation catalyst for use in this invention that was formulated by a method consistent with that of an alkylation catalyst. The starting material for the mordenite-containing catalyst was the hydrogen form of a mordenite having a molar ratio of silica:alumina of 18, hereinafter referred to as the starting mordenite. 50 parts by weight of the starting mordenite were mixed with 50 parts by weight of alumina powder. An acidified peptization solution was added to the mixture. The admixture was then extruded by means known in the art. After the extrusion process, the extrudate was dried and calcined at a temperature of 538° C. (1000° F.).

EXAMPLE 2

Example 2 illustrates preparation of a fluorided silica-alumina catalyst for use in this invention. The fluorided silica-alumina catalyst was prepared in a manner substantially similar to that described in U.S. Pat. No. 5,344,997. The weight ratio of silica per alumina, that is the weight ratio of $SiO_2$ per $Al_2O_3$, was 3:1, the fluoride content was 2.8 wt-% based on the volatile-free finished silica-alumina catalyst, and the sodium content was 0.09 wt-%.

EXAMPLE 3

An olefinic feedstock was prepared by mixing equal proportions of a blend containing olefins and of a mixture prepared from a sample of a stream containing olefins and paraffins from a commercial LAB process and normal hexane. The distributions of olefins in the blend and mixture were as shown

TABLE 1

Distribution of Olefins in Blend

| Olefin Component | Content (wt-%) |
|---|---|
| Lights[1] | 3.48 |
| normal decene | 0.051 |
| methyl undecene | 14.29 |
| normal undecene | 9.12 |
| methyl dodecene | 19.61 |
| normal dodecene | 11.09 |
| methyl tridecene | 12.37 |
| normal tridecene | 2.36 |
| $C_{14}$+ olefins | 1.12 |
| Heavies[2] | 0.3 |
| Others[3] | 26.21 |
| Total | 100 |

[1]Lights include olefins having fewer than 10 carbon atoms.
[2]Heavies include olefin dimers and trimers.
[3]Other alkyl olefins include dimethyl, trimethyl, and other olefins

TABLE 2

Distribution of Olefins in Mixture

| Olefin Component | Content (wt-%) |
|---|---|
| Lights[1] | <0.9 |
| normal decene | 9.5 |
| normal undecene | 35.3 |
| normal dodecene | 31.0 |
| normal tridecene | 23.3 |
| normal tetradecene | 0.9 |
| Total | 100 |

[1]Lights include olefins having fewer than 10 carbon atoms.

The olefinic feedstock was mixed with benzene to produce a combined feedstock consisting of 52.2 wt-% benzene, 2.8 wt-% nonnormal olefins, and 3.0 wt-% normal olefins. A first cylindrical reactor, which has an inside diameter of 0.875 in (22.2 mm), was loaded with a volume of the extrudate prepared in Example 1. A second cylindrical reactor, which has an inside diameter of 0.5 in (12.7 mm), was loaded with the catalyst prepared in Example 2 to one-third of the volume of extrudate loaded in the first reactor. The first and second reactors were connected in a series flow arrangement so that the entire effluent of the first reactor flowed to the inlet of the second reactor.

Once connected in this arrangement, the reactors were subjected to a series of 48-hour alkylation-regeneration cycles. Each cycle began with a 24-hour alkylation step, during which the combined feedstock passed to the inlet of the first reactor at a specified feed rate in order to achieve a LHSV of 1.0 $hr^{-1}$ based on the volume of extrudate in the first reactor. Each of the two reactors operated at a total pressure of 500 psi(g) (3447 kPa(g)). The inlet temperatures of the first and second reactors were adjusted to the desired temperatures for the alkylation step of the cycle. In the case of the first reactor, the desired inlet temperature for the alkylation step of each cycle was 150° C. (302° F.). In the case of the second reactor, the desired inlet temperature for the alkylation step was 50° C. (122° F.) in Cycle 1, 175° C. (347° F.) in Cycle 2, 200° C. (392° F.) in Cycle 3, and 225° C. (437° F.) in Cycle 4. During the initial 6 hour period of the alkylation step the reactors lined out. Then a selective liquid product was collected from the outlet of the second reactor during and over each of the second, third, and fourth 6-hour periods. At the end of the fourth 6-hour period, the flow to the inlet of the first reactor was switched from the combined feedstock to benzene, the alkylation step ended, and a 24-hour regeneration step began. During the regeneration step, benzene passed to the inlet of the first reactor at a rate to achieve a LHSV of 2.0 $hr^{-1}$ based on the volume of extrudate in the first reactor and at a total pressure of 500 psi(g) (3447 kPa(g)) in the two reactors. The reactor inlet temperatures during the regeneration step were the same as those used in the prior alkylation step during the initial 4-hour period of the regeneration step, were raised to 250° C. (482° F.) over the next 4-hour period, were held at 250° C. (482° F.) for an 8-hour period, and then were cooled to the desired temperatures for the alkylation step of the next cycle over the final 8-hour period. At the end of the 8-hour cooling period, the flow to the inlet of the first reactor was switched from benzene to the combined feedstock, the regeneration step ended, and another alkylation step began, thereby ending one alkylation-regeneration cycle and starting the next cycle.

The selective liquid product was analyzed by $^{13}C$ nuclear magnetic resonance (NMR) in order to determine the selectivity of the alkylation step to nonquaternary 2-phenyl-alkanes and end quaternary phenyl-alkanes. The NMR analytical method typically consists of the following. A 0.5 g sample of phenyl-alkane mixture is diluted to 1.5 g with anhydrous deuterated chloroform. A 0.3 milliliter aliquot of the diluted phenyl-alkane mixture is mixed with 0.3 milliliter of 0.1 M chromium (III) acetylacetonate in deuterated chloroform in a 5 mm NMR tube. A small amount of tetramethylsilane (TMS) is added to the mixture as a 0.0 ppm chemical shift reference. The spectrum is run on a Bruker ACP-300 FT-NMR spectrometer, which is available from Bruker Instruments, Inc., Billerica, Mass., USA. The carbon spectrum is run at a field strength of 7.05 Tesla or 75.469 MHz in a 5 mm QNP probe with a sweep width of 22727 Hz (301.1 ppm) and about 65000 data points are collected. The quantitative carbon spectrum is obtained using gated on-acquisition $^1H$ decoupling (inverse gated decoupling). The quantitative $^{13}C$ spectrum is run with 7.99 microsecond (90°) pulses, 1.442 second acquisition time, a 5 second delay between pulses, a decoupler power, using composite pulse decoupling (CPD), of 18 H with a pulse width of 105 microseconds (90°) and at least 2880 scans. The number of scans used depends on whether benzene is stripped from the liquid product prior to taking the above-mentioned 0.5 g sample. The data processing is done with the Bruker PC software WINNMR-1D, Version 6.0, which is also available from Bruker Instruments, Inc. During data processing a line broadening of 1 Hz is applied to the data. Specific peaks are integrated in the region between 152 ppm and 142 ppm. The $^{13}C$ NMR peak identifications of the chemical shifts of the benzylic carbon of the phenyl-alkane isomers is shown in Table 3. As used herein, the term "benzylic carbon" means the carbon in the ring of the phenyl group that is bound to the aliphatic alkyl group.

TABLE 3

$^{13}$C NMR Peak Identifications

| CHEMICAL SHIFT OF THE BENZYLIC CARBON (PPM) | PHENYL-ALKANE ISOMER | TYPE OF QUAT[1] |
|---|---|---|
| 149.6 | 2-methyl-2-phenyl | End |
| 148.3 | 4-methyl-2-phenyl | NQ |
|  | m-methyl-m-phenyl, m > 3 | Internal |
| 148.0 | 5-methyl-2-phenyl | NQ |
| 147.8 | m-methyl-2-phenyl, m > 4 | NQ |
|  | 2-phenyl (linear) | NQ |
|  | 3-methyl-3-phenyl | Internal |
| 147.6 | 4-methyl-2-phenyl | NQ |
| 147.2 | 3-methyl-2-phenyl | NQ |
| 146.6 | 3-methyl-2-phenyl | NQ |
| 146.2–146.3 | m-methyl-4-phenyl, m ≠ 4 | NQ |
| 145.9–146.2 | 6-methyl-3-phenyl | NQ |
| 145.9 | m-methyl-3-phenyl, m > 5 | NQ |

[1]NQ = Nonquat

The peak at 148.3 ppm is identified both with 4-methyl-2-phenyl-alkanes and with m-methyl-m-phenyl-alkanes (m>3). However, when the m-methyl-m-phenyl-alkanes (m>3) are present at more than 1%, they are seen as a distinct peak at 0.03 ppm upfield of the peak for the 4-methyl-2-phenyl-alkanes. The peak at 147.8 ppm is considered herein to be identified with the 2-phenyl-alkanes as shown in Table 3, with possible interference from 3-methyl-3-phenyl-alkanes.

The end quaternary phenyl-alkane selectivity of the alkylation step is computed by dividing the integral of the peak at 149.6 ppm by the sum of the integrals of all of the peaks listed in Table 3, and multiplying by 100. The nonquaternary 2-phenyl-alkane selectivity of the alkylation step is computed by dividing the sum of integrals of the peaks from 148.3 to 146.6 ppm by the sum of the integrals of all of the peaks listed in Table 3, and multiplying by 100, since it is assumed that the amount of internal quaternary phenyl-alkanes contributing to the peaks at 148.3 ppm and 147.8 ppm is less than about 2%.

The results of these analyses are shown in Table 4.

TABLE 4

| Cycle | Second Reactor Inlet Temperature ° C. (° F.) | Average End Quaternary Phenyl-Alkane Selectivity | Average Nonquaternary 2-Phenyl-Alkane Selectivity |
|---|---|---|---|
| 1 | 50 (122) | 9.4 | 78.3 |
| 2 | 175 (347) | 10.3 | 76.2 |
| 3 | 200 (392) | 3.8 | 76.9 |
| 4 | 225 (437) | 2.5 | 70.5 |

Cycle 1 is a base case, since its second reactor inlet temperature is so low that no significant reactions occur to any appreciable extent in the second reactor. Thus, the results of Cycle 1 are representative of those of a single reactor containing a mordenite catalyst operating at the conditions of the first reactor. In particular, Cycle 1 shows a relatively high nonquaternary 2-phenyl alkane selectivity, which is desirable, but also a relatively high end quaternary phenyl-alkane selectivity, which is undesirable. In comparison, Cycles 2–4 show the effect of using the second reactor containing a fluorided silica-alumina catalyst. The second reactor has the desirable effect of significantly decreasing the end quaternary phenyl-alkane selectivity by a factor of between 2 and 4, while decreasing the nonquaternary 2-phenyl-alkane selectivity by only about 8 or less percentage points. In addition, the results in Table 4 indicate that, for a given first reactor inlet temperature, the second reactor inlet temperature can be chosen to achieve a suitably low end quaternary phenyl-alkane selectivity and a suitably high nonquaternary 2-phenyl-alkane selectivity. A second reactor inlet temperature in the range of 175–225° C. (347–437° F.), or possibly 190–210° C. (374–410° F.) may achieve this.

What is claimed is:

1. A process for producing phenyl-alkanes, the process comprising:
   a) contacting an aryl compound and a monoolefin having from about 8 to about 28 carbon atoms, 3 or 4 primary carbon atoms, and no quaternary carbon atoms, with a first catalyst comprising mordenite operating at first reaction conditions sufficient to alkylate the aryl compound with the monoolefin and thereby form a phenyl-alkane, and recovering a first reaction product comprising the phenyl-alkane; and
   b) contacting the first reaction product with a second catalyst comprising silica-alumina operating at second reaction conditions, and recovering from the process a second reaction product comprising a phenyl-alkane having one aryl portion and one aliphatic alkyl portion containing from about 8 to about 28 carbon atoms; wherein the phenyl-alkane in the second reaction product has 2, 3, or 4 primary carbon atoms and no quaternary carbon atoms except for any quaternary carbon atom bonded by a carbon-carbon bond with a carbon atom of the aryl portion; and wherein the process has an overall selectivity to nonquaternary 2-phenyl-alkanes of from 40 to 100 and an overall selectivity to end quaternary phenyl-alkanes of less than 10 based on the second reaction product.

2. The process of claim 1 further characterized in that the first reaction conditions comprise a pressure sufficient to maintain at least partial liquid phase or supercritical conditions and a temperature of from about 80 to about 200° C.

3. The process of claim 1 further characterized in that the first reaction conditions comprise a molar ratio of aryl compound per monoolefin of from about 1:1 to about 50:1.

4. The process of claim 1 further characterized in that the mordenite has a molar ratio of silica:alumina of from 12:1 to about 90:1.

5. The process of claim 1 further characterized in that the second reaction conditions comprise a pressure sufficient to maintain at least partial liquid phase or supercritical conditions and a temperature of from about 175 to about 225° C.

6. The process of claim 1 further characterized in that the second reaction conditions comprise a molar ratio of aryl compound per monoolefin of from about 1:1 to about 50:1.

7. The process of claim 1 wherein the second catalyst comprises fluorided silica-alumina.

8. The process of claim 1 wherein the second catalyst has a weight ratio of silica per alumina of from about 0.5:1 to about 9:1.

9. The process of claim 1 wherein the aliphatic alkyl portion has from 10 to 15 carbon atoms.

10. The process of claim 1 wherein the monoolefin comprises a monomethyl-alkene.

11. The process of claim 1 further characterized in that the first reaction product comprises an end quaternary phenyl-alkane.

12. The process of claim 11 further characterized in that the second reaction conditions are sufficient to isomerize the end quaternary phenyl-alkane to a nonquaternary 2-phenyl-alkane.

13. The process of claim 12 further characterized in that the second reaction conditions are sufficient to crack the end quaternary phenyl-alkane.

14. The process of claim 11 further characterized in that the second reaction conditions are sufficient to crack the end quaternary phenyl-alkane.

15. The process of claim 11 wherein the overall selectivity to nonquaternary 2-phenyl-alkanes is denoted $N_o$ and the overall selectivity to end quaternary phenyl-alkanes is denoted $E_o$ and further characterized in that the contacting and recovering in (a) of claim 1 has an intermediate selectivity to nonquaternary 2-phenyl-alkanes denoted $N_i$ and an intermediate selectivity to end quaternary phenyl-alkanes denoted $E_i$ based on the first reaction product, and that the quotient $(E_{i-Eo})/(E_i)$ is greater than the quotient $(N_i-N_o)/(N_i)$.

16. The process of claim 11 wherein the overall selectivity to end quaternary phenyl-alkanes is denoted $E_o$ and further characterized in that the contacting in (a) of claim 1 has an intermediate selectivity to end quaternary phenyl-alkanes denoted $E_i$ based on the first reaction product, and that $E_o$ is less than $E_i$.

17. The process of claim 1 further characterized in that the monoolefin contacts the second catalyst.

18. The process of claim 1 further characterized in that the first reaction product comprises the monoolefin.

19. The process of claim 1 further characterized in that the aryl compound contacts the second catalyst.

20. The process of claim 1 further characterized in that no monoolefin contacts the second catalyst.

21. The process of claim 1 further characterized in that a first reaction zone contains the first catalyst, wherein the recovering of the first reaction product further comprises recovering from the first reaction zone a first product stream comprising the first reaction product, wherein the contacting of the first reaction product with the second catalyst further comprises contacting a first aliquot portion of the first product stream with the second catalyst, and further characterized in that a second aliquot portion of the first product stream is recycled to the first reaction zone.

22. The process of claim 1 further characterized in that a second reaction zone contains the second catalyst, wherein the recovering of the second reaction product further comprises recovering from the second reaction zone a second product stream comprising the second reaction product and recovering from the process the phenyl-alkane in the second product stream in a first aliquot portion of the second product stream, and further characterized in that a second aliquot portion of the second product stream is recycled to the second catalyst.

23. The process of claim 22 further characterized in that a third aliquot portion of the second product stream is recycled to the first catalyst.

24. The process of claim 1 wherein the recovering of the first reaction product further comprises recovering a first product stream comprising the first reaction product, wherein the contacting of the first reaction product with the second catalyst further comprises contacting a first aliquot portion of the first product stream with the second catalyst, and further characterized in that the phenyl-alkane in the first product stream is recovered from the process in a second aliquot portion of the first product stream.

25. A process for producing arylalkanes, the process comprising:
   a) contacting an aryl compound and monoolefins with a first catalyst comprising mordenite operating at first reaction conditions sufficient to alkylate the aryl compound with the monoolefins, and recovering a first reaction product comprising arylalkanes; and
   b) contacting the first reaction product with a second catalyst comprising fluorided silica-alumina operating at second reaction conditions and recovering from the process a second reaction product comprising arylalkanes having one aryl group and one aliphatic alkyl group, wherein the arylalkanes in the second reaction product have:
      (i) an average weight of the aliphatic alkyl groups of the arylalkanes of between the weight of a $C_{10}$ aliphatic alkyl group and a $C_{13}$ aliphatic alkyl group;
      (ii) a content of arylalkanes having the phenyl group attached to the 2- and/or 3-position of the aliphatic alkyl group of greater than 55 wt-% of the arylalkanes; and
      (iii) an average level of branching of the aliphatic alkyl groups of the arylalkanes of from 0.25 to 1.4 alkyl group branches per arylalkane molecule when the sum of the contents of 2-phenyl-alkanes and 3-phenyl-alkanes is more than 55 wt-% and less than or equal to 85 wt-% of the arylalkanes, or an average level of branching of the aliphatic alkyl groups of the arylalkanes of from 0.4 to 2.0 alkyl group branches per arylalkane molecule when the sum of the concentrations of 2-phenyl-alkanes and the 3-phenyl-alkanes is greater than 85 wt-% of the arylalkanes; and wherein the aliphatic alkyl groups of the arylalkanes comprise linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise methyl group branches, ethyl group branches, or propyl group branches, and wherein the alkyl group branches if any attach to any position on the aliphatic alkyl chain of the aliphatic alkyl groups provided that arylalkanes having at least one quaternary carbon atom on the aliphatic alkyl group comprise less than 20% of the arylalkanes;
   c) recovering arylalkanes from second reaction product.

* * * * *